United States Patent [19]
Parkinson et al.

[11] Patent Number: 5,095,099
[45] Date of Patent: Mar. 10, 1992

[54] FLUORESCENT COMPOUNDS FOR ABSORPTION AND RE-EMISSION OF RADIATION

[75] Inventors: Bruce A. Parkinson, Hockessin, Del.; Andrew Streitwieser, Jr., Berkley, Calif.; Douglas W. Wiley, Wilmington, Del.

[73] Assignee: E. I. Du Pont de Nemours and Company, Wilmington, Del.

[21] Appl. No.: 625,130

[22] Filed: Dec. 10, 1990

[51] Int. Cl.$^5$ .................... C07F 15/00; H01L 31/041
[52] U.S. Cl. .................... 534/15; 568/326; 568/732; 422/56; 436/800; 252/301.16; 136/247
[58] Field of Search .................. 534/15; 568/326, 732; 422/56; 436/800; 252/301.13; 136/247

[56] References Cited

U.S. PATENT DOCUMENTS

| | | | |
|---|---|---|---|
| 3,426,212 | 2/1969 | Klaas | 250/226 |
| 3,484,606 | 12/1969 | Masi | 250/71 |
| 3,865,879 | 2/1975 | Eiglmeier | 568/326 |
| 3,912,931 | 10/1975 | Gravisse et al. | 250/458 |
| 4,110,123 | 8/1978 | Goetzberger | 136/89 HY |
| 4,149,902 | 4/1979 | Mauer et al. | 136/89 PC |
| 4,175,980 | 11/1979 | Davis et al. | 136/89 FC |
| 4,440,693 | 4/1984 | Naarmann et al. | 556/34 |
| 4,492,778 | 1/1985 | Claussen et al. | 523/137 |
| 4,572,803 | 2/1986 | Yamazoe et al. | 534/16 |
| 4,803,161 | 2/1989 | Babb et al. | 436/800 X |
| 4,812,393 | 3/1989 | Goswami et al. | 422/56 |
| 4,812,409 | 3/1989 | Babb et al. | 436/800 X |

FOREIGN PATENT DOCUMENTS 390181A 3/1989 European Pat. Off. .
1388417 2/1972 United Kingdom .
87/04716 8/1987 World Int. Prop. O. .

OTHER PUBLICATIONS

Fieser, Louis F., J. Am. Chem. Soc., 1931, 53, 3456–60.
Calderbank, A. et al., J. Chem. Soc., 1954, 1285.
Haddon, R. C., J. Org. Chem. 1981, 46, 4587–88.
Weber, W. H., et al., Applied Optics, 1976, 15, 2299–2300.
Levitt, J. A., et al., Applied Optics, 1977, 16, 2684–89.
Neidlein, R., et al., Chem.-Ztg. 1976, 100, 388–9.

*Primary Examiner*—Robert L. Stoll
*Assistant Examiner*—Chhaya Sayala

[57] ABSTRACT

This invention concerns novel fluorescent compositions having the potential for absorption of visible and UV radiation and for re-emitting the radiation at longer wavelengths. The compositions comprise rare earth chelates containing a phenalenone nucleus.

17 Claims, 5 Drawing Sheets

FLUORESCENT COMPOUNDS FOR ABSORPTION AND RE-EMISSION OF RADIATION

BACKGROUND OF THE INVENTION

1. Field of the Invention

This invention concerns novel fluorescent compositions having the potential for absorption of visible and UV radiation and for re-emitting the radiation at longer wavelengths. The compositions comprise chelates containing a phenalenone nucleus. The compositions of this invention are useful as solar concentrators, liquid and solid state lasers, phosphors and wavelength shifters for optical communication.

2. Background Art

G.B. 1,388,417 covers the preparation of dyestuffs with the substituted phenalenone nucleus of the present invention.

Calderbank, A., et al., J. Chem. Soc., 1954, 1285 covers the preparation of 4,9-dihydroxyperylene-3,10-quinone.

Haddon, R. C., J. Org. Chem. 1981, 46, 4587-88 covers the preparation of methyl substituted phenalenones.

Weber, W. H. and Lambe, J., Applied Optics, 1976,15 2299-2300 describes the construction of a luminescent solar collector.

Levitt, J. A. and Weber, W. H. Applied Optics 1977, 16, 2684-89 describes the construction and materials for a luminescent greenhouse collector.

WO 87/04716 describes a photovoltaic cell and wavelength shifting device based on a dihydropyridine condensation product chelated to a lanthanide metal ion.

Neidlein, R. and Bahzadi, Z., Chem.-Ztg. 1976, 100, 388-9 synthesizes and determines the properties of Ni, Cu, Mn, Zn, Co and Fe chelates of 9-hydroxyphenalenone.

SUMMARY OF THE INVENTION

The present invention relates to novel fluorescent compositions comprising chelates containing a phenalenone nucleus of the following formula:

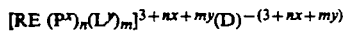

wherin:
x and y represent the formal charges on P and L;
n=1-4;
m=0-6 where $2n+m \leq 9$;
RE is a metal of the rare earth series in the $+3$ oxidation state;
L is a ligand, coordinated (mono- or polydentate) or noncoordinated, such as halide, phosphite, $\beta$-diketonate or an anion derived from ethylene diamine tetraacetic acid; and
P is an anion of a substituted hydroxy phenalenone of the formula:

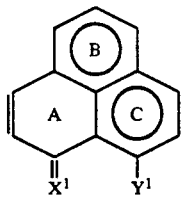

Formula I where X' is oxygen, sulfur or NR' and Y' is hydroxyl, sulfoxyl or NHR' where R' is hydrogen or an optionally substituted hydrocarbon radical, and the rings A,B and C may be further substituted with substituents which may be charged. P may also have bisfunctionality or may contain more than one hydroxy ketone functionality which can result in more than one RE or P per molecule and result in dimeric or polymeric complexes. D is present where the complex has a net charge. D is a counterion of the opposite charge from that of the complex (if the final complex retains a charge).

DETAILED DESCRIPTION OF THE INVENTION

The present invention relates to novel fluorescent compositions comprising chelates containing a phenalenone nucleus of the following formula:

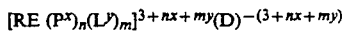

wherein:
x and y represent the formal charges on P and L;
n=1-4;
m=0-6 where $2n+m \leq 9$;
RE is a metal of the rare earth series in the $+3$ oxidation state;
L is a ligand, coordinated (mono- or polydentate) or noncoordinated, such as halide, phosphite, $\beta$-diketonate or an anion derived from ethylene diamine tetraacetic acid; and
P is an anion of a substituted hydroxy phenalenone of the formula:

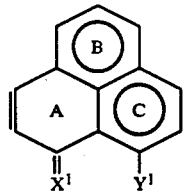

Formula I where X' is oxygen, sulfur or NR' and Y' is hydroxyl, sulfoxyl or NHR' where R' is hydrogen or an optionally substituted hydrocarbon radical, and the rings A, B and C may be further substituted with substituents which may be charged. P may also have bisfunctionality or may contain more than one hydroxy ketone functionality which can result in more than one RE or P per molecule and result in dimeric or polymeric complexes. D is present where the complex has a net charge. D is a counter ion of the opposite charge from that of the complex (if the final complex retains a charge).

The $+3$ rare earth metals useful in the above compositions are neodymium, holmium, dysprosium, samarium, ytterbium and mixtures thereof, preferably neodymium or mixtures containing neodymium.

The substituted hydrocarbon radicals represented by R' are preferably substituted alkyl or aryl radicals. Examples of such alkyl radicals are lower alkyls such as methyl, ethyl, n-propyl, i-propyl and n-butyl, hydroxy lower alkyls such as β-hydroxyethyl, aryl lower alkyls such as benzyl, lower alkoxy lower alkyls such as β-(methoxy or ethoxy)ethyl and β-methoxypropyl, cyano lower alkyls such a β-cyanoethyl, and lower alkoxy carbonyl lower alkyls such as β-carboethoxyethyl. Where R' is an aryl radical, the preferred aryl is phenyl and substituted derivatives such as tolyl, anisyl, chlorophenyl, bromophenyl, carboxyphenyl and sulphophenyl.

Further substituents on the rings A, B and C include lower alkyls such as methyl, lower alkoxys such as methoxy, chloro, bromo, nitro, cyano, carboxylic acid, sulfonic acid, carbamoyl and N-lower alkyl and N,N-di($C_1$ to $C_4$) derivatives thereof, sulphamoyl and N-lower alkyl and N,N-$C_1$ to $C_4$ alkyl derivatives thereof, amino, N-lower alkamino, N,N-di $C_1$ to $C_4$ alkyl amino, acylamino, such as acetylamino, propionylamino and benzoylamino and acyl amino groups chosen to impart favorable solubility and stability. In addition to the above described substituents, additional six-membered rings may be connected to the phenalenone system to create anions of poly-ring materials such as: 2,3-benzo-9-hydroxy-phenalenone (4-hydroxybenzanthrone) (1), 4,5-benzo-9-hydroxyphenalenone (2), and the dianion of 4,9-dihydroxyperylene-3,10-quinone (3).

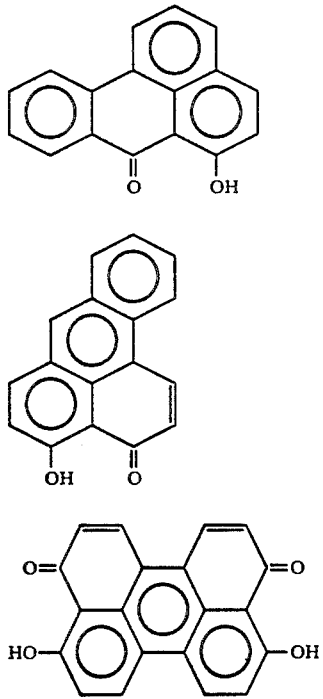

Where the terms "lower alkyl" and "lower alkoxy" are used in this specification, they denote alkyl and alkoxy radicals containing from 1 to 4 carbon atoms.

The process for the manufacture of the above described chelates comprises reacting a compound of Formula I, above, with a base to form its anion, followed by the addition of a rare earth +3 ion, in a solvent. The rare-earth ions may be used with counter ions such as, but not limited to, chloride, acetate or methoxide. The solvent must be selected so that the initial reactants are soluble in it. The bases used to prepare the anion of Formula 1 include those which are strong enough for deprotonation including, but not limited to sodium or potassium hydroxide, sodium carbonate, sodium methoxide, and organic nitrogen bases such as pyridine, triethylamine, piperidine and diazabicyclooctane (DABCO). The stoichiometry will usually determine the composition of the resulting chelate. The chelate is then isolated by filtration, if it is insoluble, or after the addition of another solvent in which the chelate is insoluble. In some applications, the isolation of the chelates is not necessary. Thus, in these applications, the chelates can be generated in situ in the reaction system where measurements can be conveniently made.

The chelates of the present invention are useful for fluorescent solar concentrators, liquid and solid state lasers, phosphors and wavelength shifters for optical communication. Light absorbed by the chelates over a range of wavelengths is emitted at a lower energy wavelength, usually over a very narrow band. These chelates emit at a wavelength which is usually far displaced from their absorption so that little, if any, self absorption occurs. This is in contrast to the usual "Stokes Shift" observed in the florescence of an organic dye, where a large portion of the emission is self absorbed. Thus, the efficiency of useful energy transference is greatly enhanced.

The compositions of the present invention can be used in a fluorescent solar collector where a substrate such as a plastic plate or film containing a low concentration of one or more novel chelates (e.g., neodymium chelates) of different phenalenone dyes is irradiated with sunlight. The configuration of the substrate in the form of a thin film or plate results in most internally emitted light being emitted at the edges of the film or plate. In the preferred configuration, the side opposite that of illumination is modified to be a diffuse reflector and several edges of the device may be mirrored such that light emits from only one edge. The absorption of the solar light results in an emission at the characteristic lanthanide wavelength which propagates to the edge where an appropriately coupled photovoltaic cell is placed so that the sunlight is converted to useful electric power. Further physical definition of these devices has been well described in various references but have lacked the improved energy conversions resulting from use of the chelates as described in this invention. The invention also results in the photo-stabilization of the chelated organic dye molecules. Thus, the observed energy transfer leads to greatly decreasing the lifetime of the dye's excited state so that the usually competitive photodegradation pathways are not as frequent.

Figure 1:
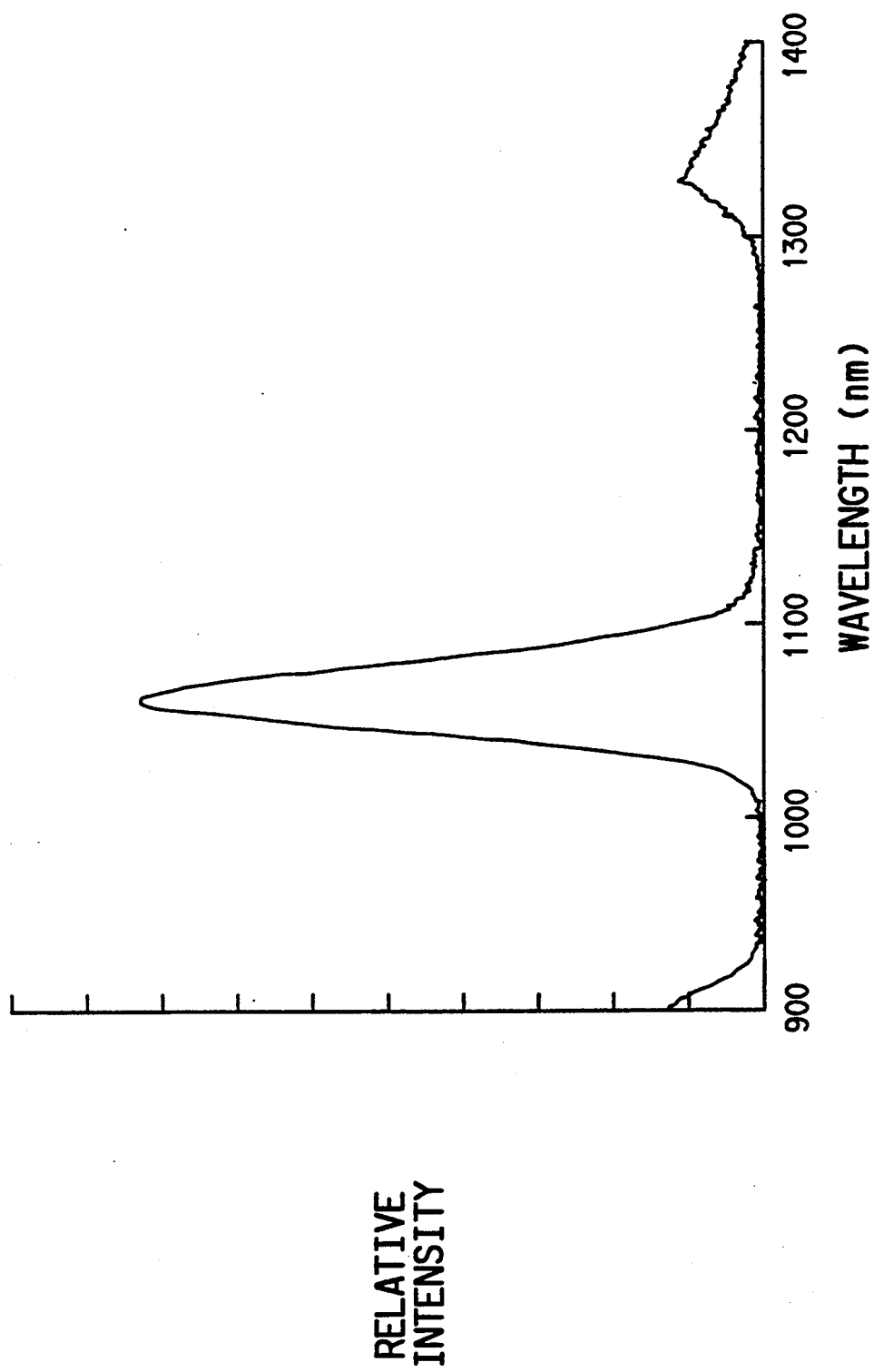
FIG. 1 is the emission spectrum of the chelate Nd(9-hydroxy-1-phenalenone)$_3$.

PREPARATION OF REAGENTS a. The preferred preparation of the 9-hydroxy-1-phenalenone and 9-hydroxy-2-methyl-1-phenalenone was by reacting 2-methoxynaphthalene with trans-cinnamic acid and α-methyl cinnamic acid, respectively, in benzene with aluminum chloride and cyclizing with dephenylation the resulting product in dichloroethane with aluminum chloride. The crude products were purified by sublimation and recrystallization. This was shown in R. C. Haddon, R. Rayford, and A. M. Hirani, J. Org. Chem. 46, 4587–4588 (1981).

b. The 2,3-benzo-9-hydroxy-phenalenone or 4-hydroxybenz-anthrone was obtained by cyclization of 1-benzoyl-2-naphthol in molten aluminum chloride as shown in L. F. Fieser, J. Am. Chem. Soc., 53, 3546 (1931).

c. The 4,9-dihydroxyperylene-3,10-quinone was synthesized by heating 3,4,9,10-tetranitroperylene in concentrated sulfuric acid followed by air oxidation of a basic suspension of the resulting tetrahydroxyperylene as shown in A. Calderbank, A. W. Johnson, and A. R. Todd, J. Chem. Soc., 1285 (1954).

EXAMPLES

The invention is illustrated but not limited by the following Examples.

EXAMPLE 1

Preparation of Neodymium Chelate of 9-Hydroxy-1-phenalenone

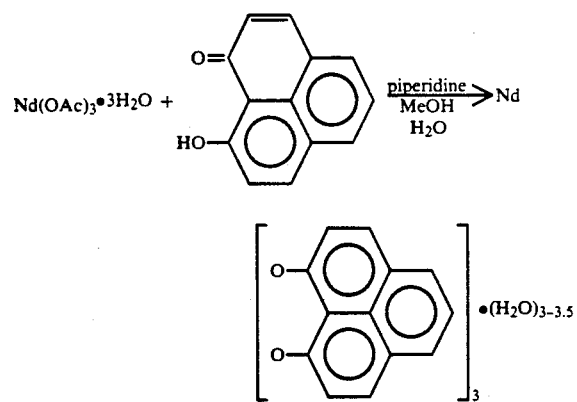

To a hot solution of 0.34 g (1 mmol) of neodymium acetate hydrate in 100 mL of methanol and 7 mL of water was added 0.59 mL (6 mmol) of piperidine followed by 0.79 g (4 mmol) of 9-hydroxy-1-phenalenone dissolved in 50 mL of methanol and 3 mL of water with stirring. The yellow precipitate which formed was digested for 10 min then allowed to cool to room temperature followed by cooling in an ice bath. The neodymium chelate was collected, washed with cold $CH_3OH/H_2O$ (15:1) and 3×50 mL of cold MeOH then air dried to give 0.47 g as an orange-yellow powder. The $MeOH/H_2O$ solution was concentrated to give recovered 9-hydroxy-1-phenalenone. An additional 0.08 g of the neodymium chelate were recovered from the MeOH washes for a yield of 70%. The crude product was recrystallized twice from dimethylsulfoxide:$H_2O$ (9:1 by volume), dissolving first in hot DMSO; 15 mL per 0.1 g solid. The yellow solid, no mp below 350° C., was dried in vacuum at 130° C. Analyses indicate three molecules of the hydroxyphenalenone anion are chelated to one neodymium with 3–3.5 moles of water. Calculated for $Nd(C_{13}H_7O_2)_3(H_2O)_3$: C, 59.8; H, 3.5; Nd, 18.4 and for $Nd(C_{13}H_7O_2)_3(H_2O)_{3.5}$: C, 59.1; H, 3.6; Nd, 18.2. Found: C, 59.0, 59.1; H, 3.1, 3.1; Nd, 18.5, 18.7.

Fluorescent Spectral Measurements

[The spectra for Examples 1 through 4 were obtained on a Spex Model 212 Spectrofluorimeter equipped with a North Coast EO-817 Germanium detection system.]

A $5 \times 10^{-4}$ M solution in dimethylsulfoxide (DMSO) of the above Nd chelate was examined for its fluorescence and shown to emit at 1060 nm characteristic of neodymium (FIG. 1) when irradiated with 464 nm light. The excitation spectrum with the output detector set at 1060 nm is shown in FIG. 2 with a fluorescence active range of 300 to 480 nm. These emission and excitation spectra can also be obtained when the chelate is generated in situ by mixing DMSO solutions of 3 or more parts of 9-hydroxy-1-phenalenone to one part of $NdCl_3$ at $5 \times 10^{-4}$ M along with a slight excess of an organic base such as piperidine or DABCO (diazabicyclooctane).

EXAMPLE 2

Neodymium chelate of 2-methyl-9-hydroxy-1-phenalenone

Figure 2:
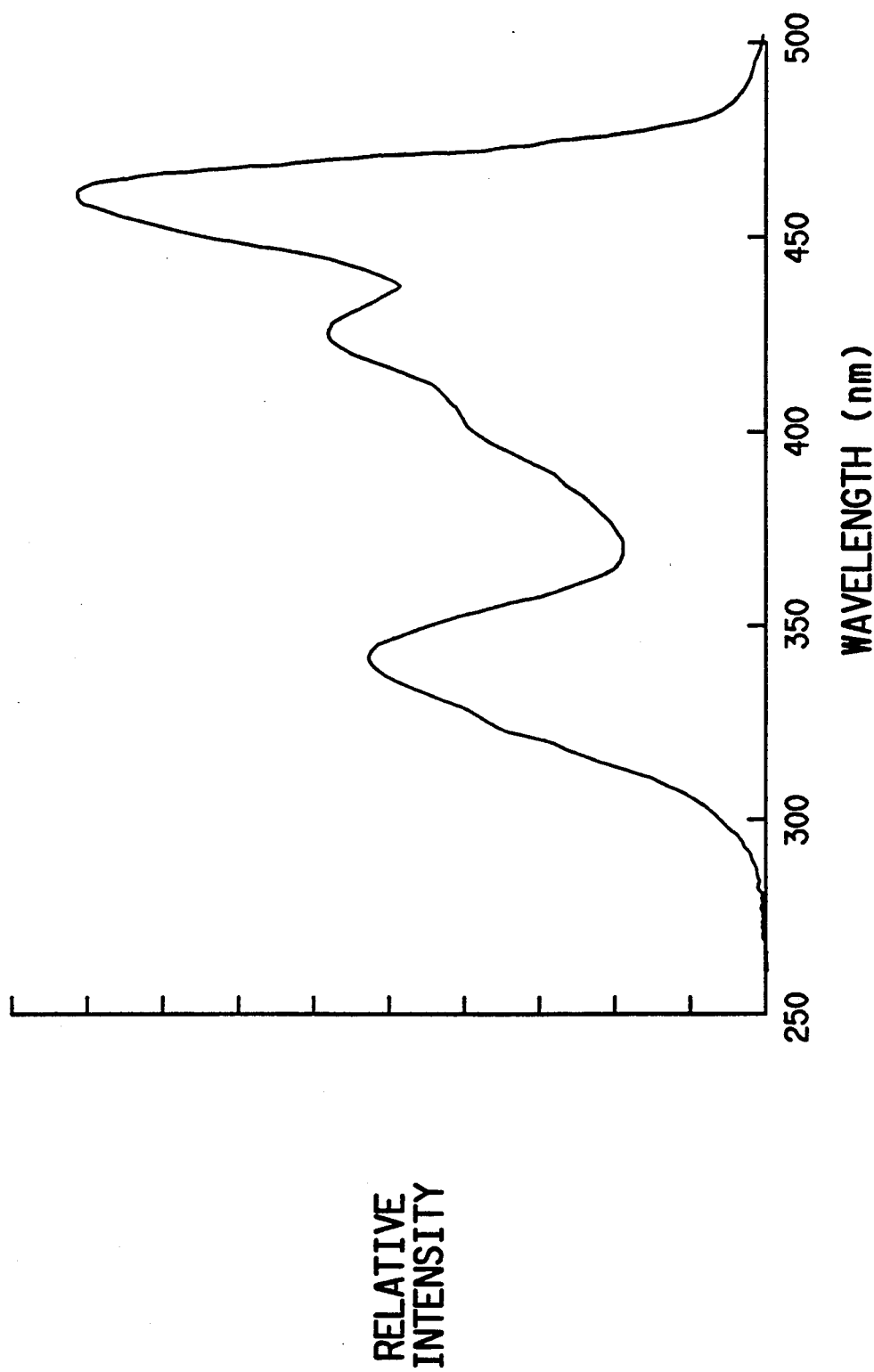
FIG. 2 is the excitation spectrum of the chelate Nd(9-hydroxy-1-phenalenone)$_3$.
Figure 3:
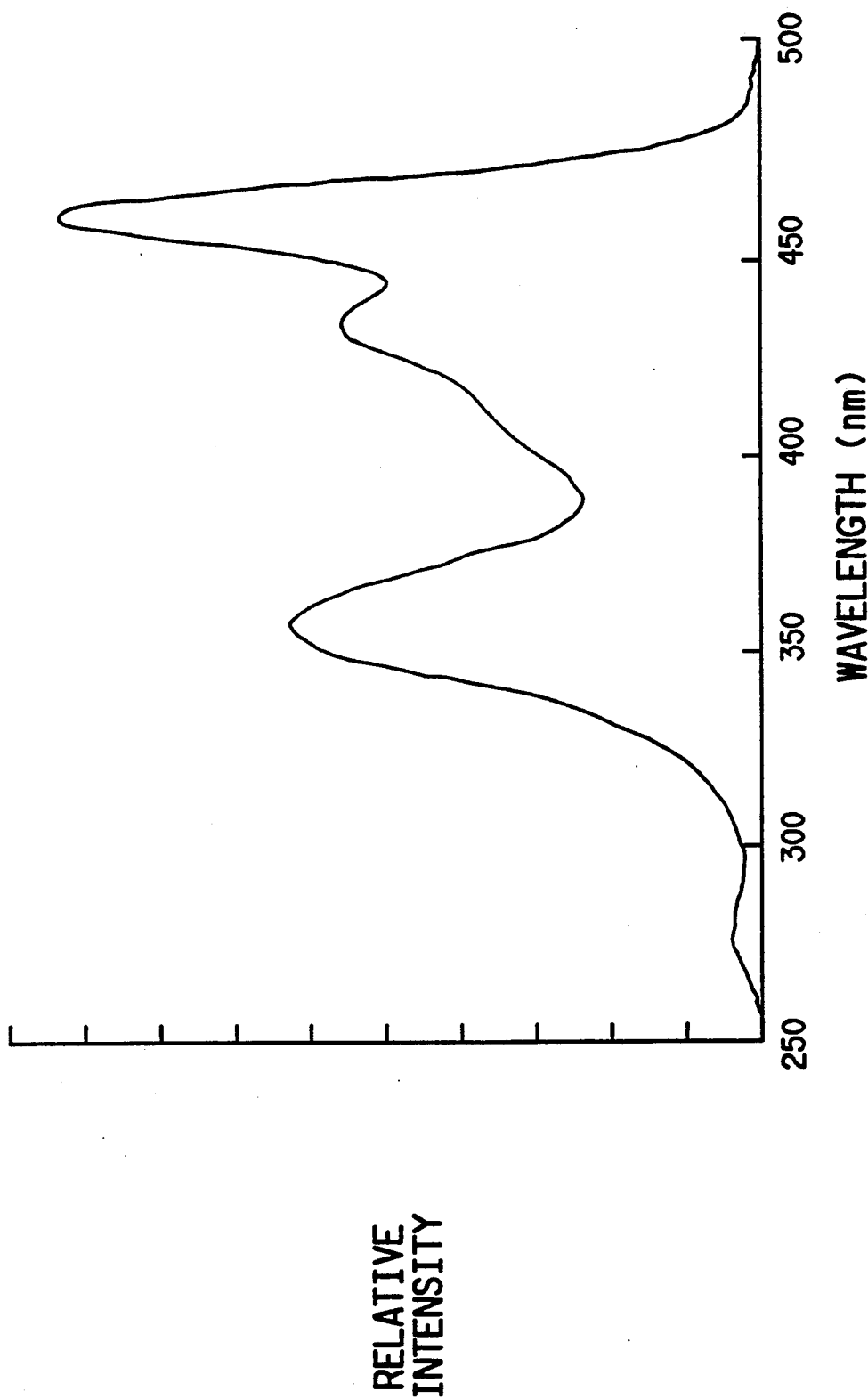
FIG. 3 is the excitation spectrum of the Nd$^{+3}$ chelate of 2-methyl-9-hydroxy-1-phenalenone.

Using the in situ method, the neodymium chelate of 2-methyl-9-hydroxy-1-phenalenone was examined for its fluorescence in DMSO and DMSO($d_6$) and shown to emit at 1060 nm, similar to that shown in FIG. 1. The excitation spectrum with the output detector set at 1060 nm is shown in FIG. 3.

EXAMPLE 3

Neodymium chelate of 2,3-benzo-9-hydroxy-1-phenalenone

Figure 4:
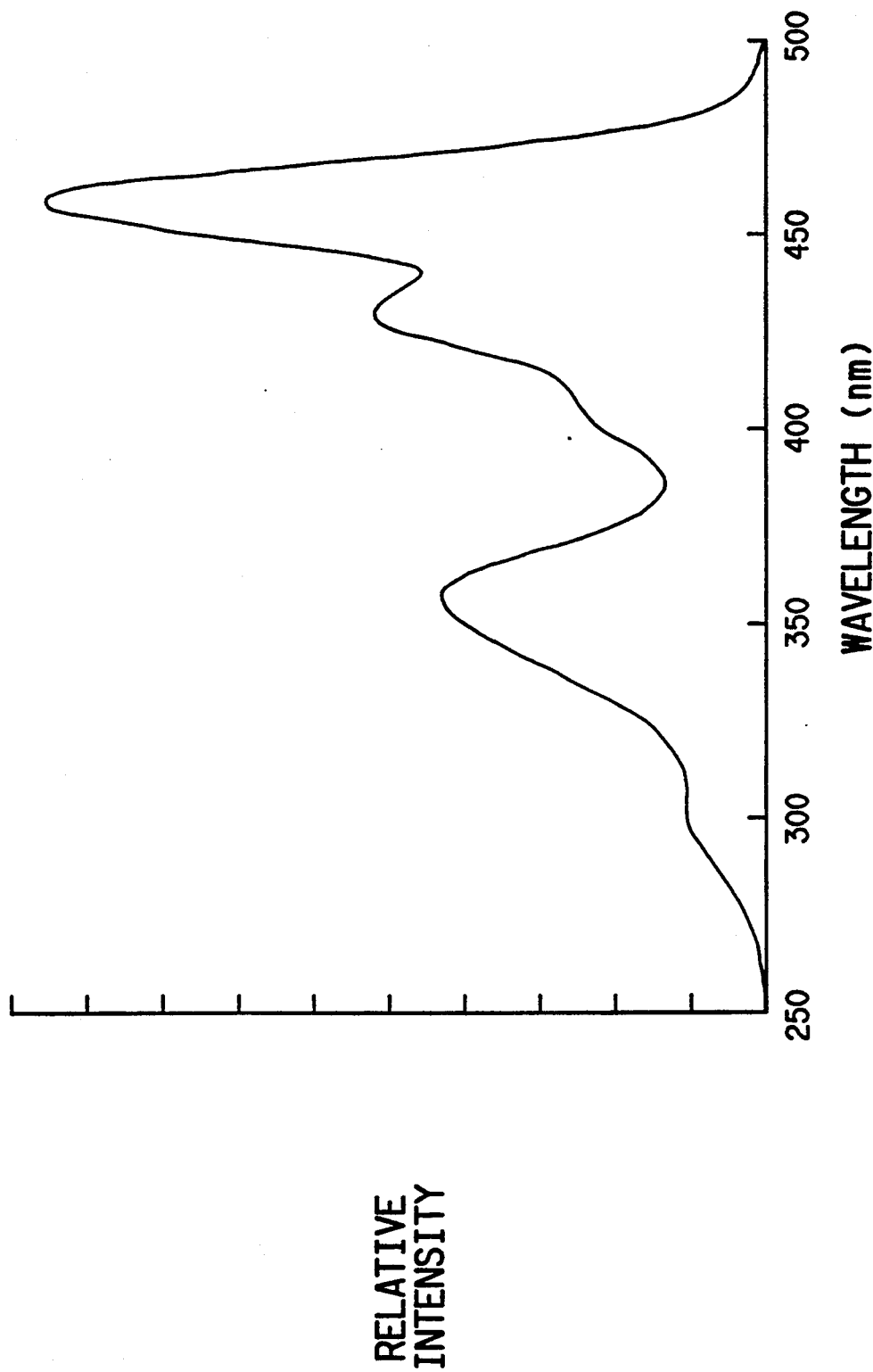
FIG. 4 is the excitation spectrum of the Nd$^{+3}$ chelate of 4-hydroxybenzanthrone.

In a similar fashion, the neodymium chelate of 2,3-benzo-9-hydroxy-phenalenone or 4-hydroxybenzanthrone in DMSO($d_6$) gave the same neodymium emission as shown in FIG. 1 and the excitation spectrum as shown in FIG. 4.

EXAMPLE 4

Neodymium chelate of 4,9-dihydroxyperylene-3,10-quinone (bis-anion)

Figure 5:
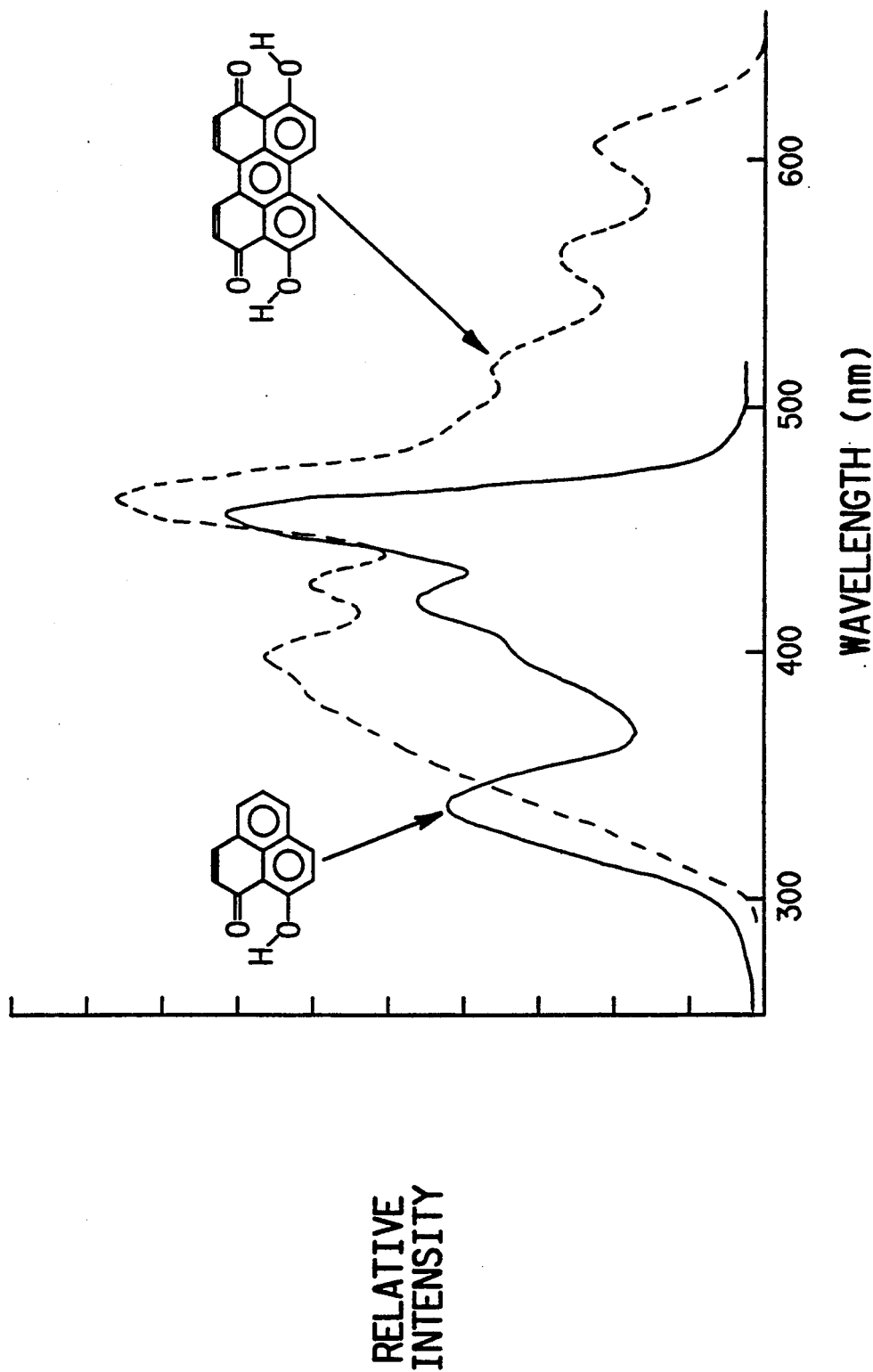
FIG. 5 is the excitation spectra of the Nd$^{+3}$ chelates of 4.9-dihydroxyperylene-3,10-quinone and 9-hydroxy-1-phenalenone.

Similarly the neodymium chelate of 4,9-dihydroxyperylene-3,10-quinone in DMSO($d_6$) gave the same neodymium emission as seen in FIG. 1 and the excitation spectrum as shown in FIG. 5. FIG. 5 also shows the excitation spectrum of the neodymium chelate of the 9-hydroxy-1-phenalenone to demonstrate the dramatic increase of the fluorescence active range to the red (300 to 650 nm) by the perylene bis-chelate.

As many differing embodiments of this invention may be made without departing from the spirit and scope thereof, it is to be understood that this invention is not limited to the specific embodiments exemplified except as defined by the appended claims.

We claim:

1. A fluorescent composition comprising a chelate of the following formula:

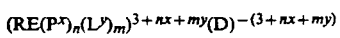

wherein:

x and y are the formal charges on P and L;
n=1-4;
m=0-6 where 2n+m≦9;
RE is a metal of the rare earth series in the +3 oxidation state;
L is a mono- or polydenate ligand, coordinated or noncoordinated; and
P is an anion of the formula:

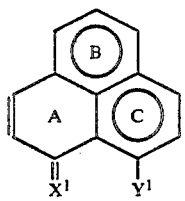

Formula I where X' is oxygen, sulfur or NR' and Y' is hydroxyl, sulfoxyl or NHR' where R' is a hydrogen or an optionally substituted hydrocarbon radical, and the rings A, B and C are optionally further substituted with substituents and an optional counterion D.

2. The composition of claim 1 wherein substituents on the rings A, B and C are independently selected from $C_1$ to $C_4$ alkyl, $C_1$ to $C_4$ alkoxy, chloride, bromide, nitro, cyano, carboxylic acid, sulfonic acid, carbamoyl and N-$C_1$ to $C_4$ alkyl and N,N-di($C_1$ to $C_4$) derivatives thereof, sulphamoyl and N-$C_1$ to $C_4$ alkyl and N,N-$C_1$ to $C_4$ alkyl derivatives thereof, amino, N-$C_1$ to $C_4$ alkamino, N,N-di $C_1$ to $C_4$ alkyl amino, acylamino, acyl amino groups and six-membered rings.

3. The composition of claim 1 wherein substituted hydrocarbon radicals represented by R' are alkyl or aryl or substituted alkyl or aryl radicals.

4. The composition of claim 3 where R' is an alkyl radical.

5. The composition of claim 4 wherein R' is an alkyl radical selected from lower alkyls, hydroxy lower alkyls, aryl lower alkyls, cyano lower alkyls, and lower alkoxy carbonyl lower alkyls.

6. The composition of claim 3 wherein R' is an aryl radical.

7. The composition of claim 6 wherein R' is selected from phenyl, tolyl, anisyl, chlorophenyl, bromophenyl, carboxyphenyl and sulphophenyl.

8. An ingredient on a substrate in a fluorescent solar collector comprising a chelate nucleus of the following formula:

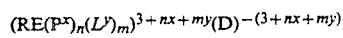

wherein:
x and y are the formal charges on P and L;
n=1-4;
m=0-6 where 2n+m≦9;
RE is a metal of the rare earth series in the +3 oxidation state;
L is a mono- or polydentate ligand, coordinated or noncoordinated; and
P is an anion of the formula:

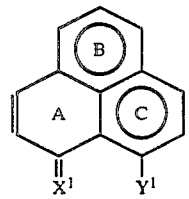

Formula I where X' is oxygen, sulfur or NR' and Y' is hydroxyl, or NHR' where R' is a hydrogen or an optionally substituted hydrocarbon radical, and the rings A, B and C are optionally further substituted with substituents and an optional counterion D.

9. The composition of claim 1 wherein RE is selected from neodymium, ytterbium and mixtures thereof.

10. The composition of claim 1 wherein RE is selected from neodymium and mixtures containing neodymium.

11. The composition of claim 1 wherein P is the dianion of 4,9-dihydroxyperlene-3,10-quinone.

12. The composition of claim 1 wherein P is an anion of 2,3-benzo-9-hydroxyphenalenone.

13. The composition of claim 1 wherein P is an anion of 4,5-benzo-9-hydroxyphenalenone.

14. The composition of claim 9 wherein RE is selected from ytterbium and mixtures containing ytterbium.

15. The composition of claim 1 wherein substituents on the rings A, B and C are charged and a suitable counterion D is present to balance the charge.

16. The composition of claim 1 wherein L is a ligand selected from halide, phosphite, β-diketonate and an anion derived from ethylene diamine tetraacetic acid.

17. The neodymium chelate of 9-hydroxy-1-phenalenone.

* * * * *